United States Patent
Sharma et al.

(10) Patent No.: US 9,084,427 B2
(45) Date of Patent: Jul. 21, 2015

(54) SAFENING FLUTHIACET-METHYL ON SORGHUM WITH 2,4-D AMINE

(71) Applicants: Shiv D. Sharma, Philadelphia, PA (US); Gail G. Stratman, Stromsburg, NE (US)

(72) Inventors: Shiv D. Sharma, Philadelphia, PA (US); Gail G. Stratman, Stromsburg, NE (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 14/381,832

(22) PCT Filed: Feb. 25, 2013

(86) PCT No.: PCT/US2013/027618
§ 371 (c)(1),
(2) Date: Aug. 28, 2014

(87) PCT Pub. No.: WO2013/130392
PCT Pub. Date: Sep. 6, 2013

(65) Prior Publication Data
US 2015/0051073 A1    Feb. 19, 2015

Related U.S. Application Data

(60) Provisional application No. 61/605,430, filed on Mar. 1, 2012.

(51) Int. Cl.
*A01N 63/00* (2006.01)
*A01N 43/90* (2006.01)
*A01N 37/38* (2006.01)

(52) U.S. Cl.
CPC ............... *A01N 43/90* (2013.01); *A01N 37/38* (2013.01)

(58) Field of Classification Search
None
See application file for complete search history.

(56) References Cited

U.S. PATENT DOCUMENTS

| | | | |
|---|---|---|---|
| 2,390,941 A | 12/1945 | Jones | |
| 4,532,732 A * | 8/1985 | Szczepanski | 504/100 |
| 4,906,279 A | 3/1990 | Yamaguchi et al. | |
| 6,939,831 B1 * | 9/2005 | Caminade et al. | 504/367 |
| 2010/0016160 A1 | 1/2010 | Bettarini et al. | |
| 2010/0197500 A1 | 8/2010 | Kikugawa et al. | |

FOREIGN PATENT DOCUMENTS

| | | | |
|---|---|---|---|
| RU | 2235463 | * | 9/2004 |
| RU | 2235463 C2 | | 9/2004 |
| SU | 1715187 | * | 2/1992 |
| SU | 1715187 A3 | | 2/1992 |

OTHER PUBLICATIONS

Ball, Jeff, Article: "Before Planting Your Grain Sorghum" [online at www.noble.org] 1997-2015 The Samuel Roberts Noble Foundation, Inc. (2 pages).

* cited by examiner

*Primary Examiner* — Alton Pryor
(74) *Attorney, Agent, or Firm* — FMC Corporation

(57) ABSTRACT

The present invention is directed to a method for controlling weeds post-emergently in *sorghum* comprising applying to such *sorghum* a herbicidally effective amount of a composition comprising (a) fluthiacet-methyl and (b) 2,4-D, wherein such 2,4-D is present in a safening amount.

11 Claims, No Drawings

SAFENING FLUTHIACET-METHYL ON SORGHUM WITH 2,4-D AMINE

FIELD OF THE INVENTION

This invention relates to a method for controlling weeds post-emergently in *sorghum* comprising applying to such *sorghum* a herbicidally effective amount of a composition comprising (a) fluthiacet-methyl and (b) 2,4-D, wherein such 2,4-D is present in a safening amount.

BACKGROUND OF THE INVENTION

One of the more preferred methods of controlling weeds in crops involves the post-emergent control of weeds wherein herbicide(s) are applied after the crop in question has emerged from the soil. Post-emergent control is desirable as it requires the application of herbicide only where an infestation of weeds is present. In contrast, pre-emergent control requires the application of herbicide early in the growing season before most weeds have germinated, with the result that such chemicals must be employed throughout a field even if they would ultimately not be needed.

Fluthiacet-methyl or methyl [[2-chloro-4-fluoro-5-[(tetrahydro-3-oxo-1H,3H-[1,3,4]thiadiazolo[3,4-α]pyridazin-1-ylidene)amino]phenyl]thio]acetate, is an effective post-emergent herbicide for a number of weeds, particularly broad leaved weeds. While such compound exhibits desirable selectivity for corn and soybeans, fluthiacet-methyl exhibits an undesirably high degree of phytotoxicity when applied to *sorghum*. Accordingly, due to concerns about the injury done to the *sorghum* itself, it has not been commercially acceptable to use such herbicide to control weeds in *sorghum*.

Thus there is a need for formulations of fluthiacet-methyl which could be employed post-emergently over *sorghum* which exhibited reduced phtotoxicity to such crop.

While 2,4-D, or 2,4-dichlorophenoxyacetic acid is employed as a post-emergent herbicide for *sorghum*, care has to be taken in the use of such herbicide in *sorghum* in order to avoid damage to the crop itself. For example, Jeff Ball in his article *Before Planting Your Grain Sorghum*, posted on the www.noble.org website cautions that "The use of . . . 2,4-D increases the risk of crop damage . . . 2,4-D should be used at low rates when the crop is less than 8 inches in height to avoid serious crop injury". Somewhat similarly, the label for Amine 4 2,4-D Weed Killer (Loveland) cautions to "Treat only after the *sorghum* is 6 inches high, and preferably before it is 15 inches high".

Applicants have now surprisingly found that adding an effective amount of 2,4-D—a herbicide which itself can cause damage to *sorghum* when employed post-emergently—significantly reduces the phytotoxic damage to *sorghum* by fluthiacet-methyl, with the result that a composition comprising 2,4-D and fluthiacet-methyl can be used to post-emergently control weeds in *sorghum* without causing an unacceptable amount of phytotoxic damage to such crop.

Even more unexpectedly, such a composition can be applied to *sorghum* at a very early growth stage (of about 4 to 6 inches) without causing excessive phytotoxic damage.

SUMMARY OF THE INVENTION

The present invention is directed to a method of controlling weeds post-emergently in *sorghum* comprising applying to such *sorghum* a herbicidally effective amount of a composition comprising (a) fluthiacet-methyl and (b) 2,4-D, wherein such 2,4-D is present in a safening amount.

DETAILED DESCRIPTION OF THE INVENTION

The present invention is directed to a method of controlling weeds post-emergently in *sorghum* comprising applying to such *sorghum* a herbicidally effective amount of a composition comprising (a) fluthiacet-methyl and (b) 2,4-D, wherein such 2,4-D is present in a safening amount.

As is employed herein, the term "safening amount" refers to an amount of 2,4-D which reduces the amount of phytotoxic damage to *sorghum* which would be caused by the application of a particular amount of fluthiacet-methyl alone.

Fluthiacet-methyl , or methyl [[2-chloro-4-fluoro-5-[tetrahydro-3-oxo-1H,3H-[1,3,4]thiadiazolo[3,4-α]pyridazin-1-ylidene)amino]phenyl]thio] acetate, is described in U.S. Pat. No. 4,906,279.

2,4-D, or 2,4-dichlorophenoxyacetic acid, is described in U.S. Pat. No. 2,390,941. 2,4-D can be employed in any of its agriculturally acceptable acid, salt or ester forms. The use of the dimethylamine salt is particularly preferred.

In the practice of the method of this invention, fluthiacet-methyl is typically employed at a rate of between 0.0025 and 0.0075 pounds per acre; and is preferably applied at a rate of between 0.0043 and 0.0064 pounds per acre. The 2,4-D is applied in an amount sufficient to safen the fluthiacet-methyl, typically at a rate of between 0.063 and 1.0 pounds per acre; and is preferably employed at a rate between 0.25 and 0.5 pounds per acre.

The mixture may be employed in the form of a tank mix or in the form of a premix. Such pre-mix may be in the form any conventionally employed agricultural formulation including dry granules, water-soluble or water-dispersible granules, dusts, wettable powders, emulsifiable concentrates, suspension concentrates and the like.

The fluthiacet-methyl and 2,4-D can be applied simultaneously or sequentially, provided that such sequential application is made within a sufficiently short period of time that the *sorghum* crop is not excessively damaged.

The method of the present invention is particularly useful for the control of weeds in grain *sorghum* (*sorghum bicolor*), although it can also be employed to control weeds in grass *sorghum* and sweet *sorghum* as well. The *sorghum* should be at a height of at least four inches at the time of application.

EXAMPLES

The following examples further illustrate the present invention, but should not be construed as in any way limiting its scope. The examples include protocols for the evaluation of the compositions of the present invention in which a beneficial effect was observed. The test compositions used were commercially available formulations of 2,4-D Amine (2,4-D Amine 4 Herbicide; available from AgriSolutions) and fluthiacet-methyl (Cadet™ Herbicide; available from FMC Corporation).

Phytotoxicity data were taken as percent control. Percent control was determined by a method similar to the 0 to 100 rating system disclosed in "Research Methods In Weed Science," 2nd ed., B. Truelove, Ed.; Southern Weed Science Society; Auburn University, Auburn, Ala., 1977. The present rating system is as follows:

| Rating Percent Control | Description of main Categories | Crop Description |
| --- | --- | --- |
| 0 | No effect | No crop reduction or injury |
| 10 | Slight effect | Slight discoloration or stunting |
| 20 | | Some discoloration, stunting or stand loss |
| 30 | | Crop injury more pronounced but not lasting |
| 40 | Moderate effect | Moderate injury, crop usually recovers |
| 50 | | Crop injury more lasting, recovery doubtful |
| 60 | | Lasting crop injury, no recovery |
| 70 | Severe effect | Heavy injury and stand loss |
| 80 | | Crop nearly destroyed, a few survivors |
| 90 | | Only occasional plants left |
| 100 | Complete effect | Complete crop destruction |

Example 1

Post-emergent Evaluation of 2,4-D Amine 4 Herbicide and Cadet™ Herbicide on Grain *Sorghum*

The test compositions of the present invention were evaluated for safening of fluthiacet-methyl on *sorghum* in the following manner:

The experimental design used randomized plots with post-emergent treatment (*sorghum vulgare*, Pioneer variety 83G19, 4 inches to 6 inches tall) and four replications per test trial. The size of each experimental plot was 9 feet by 40 feet. The application of each test composition was performed with a backpack carbon dioxide pressurized boom sprayer, calibrated to spray 15 gallons per acre. Test compositions containing fluthiacet-methyl, 2,4-D Amine and mixtures thereof were diluted with water to provide the appropriate test rate concentrations. A nonionic surfactant was added to each test treatment at a 0.25% wt/wt concentration.

The safening effect of mixtures of 2,4-D Amine and fluthiacet-methyl were evaluated in each experimental plot from 3 to 14 days after treatment (DAT) of each test rate. Untreated control plots were also included in the trials. The results, shown as an average of the replications, are summarized in Table 1 below.

TABLE 1

Percent Injury to *Sorghum*

| | | % Injury to *Sorghum* | | |
| --- | --- | --- | --- | --- |
| Treatment | Rate (lb ai/ac) | 3 DAT | 7 DAT | 14 DAT |
| Cadet™ | 0.0064 | 28 | 4 | 0 |
| Cadet™ + 2,4-D Amine | 0.0064 + 0.25 | 18 | 4 | 0 |
| Control | | 0 | 0 | 0 |

Example 2

Post-emergent Evaluation of 2,4-D Amine 4 Herbicide and Cadet™ Herbicide on Grain *sorghum* and Palmer amaranth The test compositions of the present invention were evaluated for safening of fluthiacet-methyl on *sorghum* in the following manner:

The experimental design used randomized plots with post-emergent treatment to *sorghum bicolor*, variety DKS44-2 (8 inches tall) and Palmer amaranth (*Amaranthus palmeri*), three replications per test trial. The size of each experimental plot was 15 feet by 25 feet. The application of each test composition was performed with a backpack carbon dioxide pressurized boom sprayer, calibrated to spray 10 gallons per acre. Test compositions containing fluthiacet-methyl, 2,4-D Amine and mixtures thereof were diluted with water to provide the appropriate test rate concentrations. A nonionic surfactant was added to each test treatment at a 0.25 wt % concentration.

The safening effect of mixtures of 2,4-D Amine and fluthiacet-methyl were evaluated in each experimental plot from 3 to 21 days after treatment (DAT) of each test rate. Untreated control plots were also included in the trials. The results, shown as an average of the replications, are summarized in Table 2 below.

TABLE 2

Percent Injury to *Sorghum* and Control of *Palmer amaranth*

| Treatment | Rate (lb ai/ac) | 3 DAT | 7 DAT | 15 DAT | 21 DAT |
| --- | --- | --- | --- | --- | --- |
| | | % Injury to *Sorghum* | | | |
| Cadet™ | 0.0043 | 22 | 20 | 10 | 4 |
| Cadet™ + 2,4-D Amine | 0.0043 + 0.25 | 12 | 12 | 10 | 5 |
| Cadet™ | 0.0064 | 33 | 27 | 15 | 7 |
| Cadet™ + 2,4-D Amine | 0.0064 + 0.25 | 23 | 22 | 13 | 5 |
| Control | | 0 | 0 | 0 | 0 |
| | | % Control of *Palmer amaranth* | | | |
| Cadet™ | 0.0043 | 100 | 90 | 83 | 80 |
| Cadet™ + 2,4-D Amine | 0.0043 + 0.25 | 100 | 93 | 90 | 87 |
| Cadet™ | 0.0064 | 100 | 93 | 83 | 78 |
| Cadet™ + 2,4-D Amine | 0.0064 + 0.25 | 100 | 92 | 88 | 85 |
| Control | | 0 | 0 | 0 | 0 |

As can be seen from the examples above, the addition of 2,4-D Amine to fluthiacet-methyl provides a safening affect to *sorghum* plants that are at least four inches in height at the time of application and maintaining or providing better control of Palmer amaranth.

Those of ordinary skill in the art will appreciate that variations of the invention may be used and that it is intended that the invention may be practiced otherwise than as specifically described herein. Accordingly, this invention includes all modifications encompassed within the spirit and scope of the invention as defined by the following claims.

What is claimed is:

1. A method for controlling weeds post-emergently in *sorghum* comprising applying to said *sorghum* a herbicidally effective amount of a composition comprising (a) fluthiacet-methyl and (b) 2,4-D, wherein said 2,4-D is present in a safening amount to reduce injury to *sorghum* caused by said fluthiacet-methyl.

2. The method of claim 1 wherein the fluthiacet-methyl is applied at a rate of from 0.0025 to 0.0075 pounds per acre.

3. The method of claim 1 wherein the fluthiacet-methyl is applied at a rate of from 0.0043 to 0.0064 pounds per acre.

4. The method of claim 2 wherein the 2,4-D is applied at a rate of from 0.063 to 1.0 pounds per acre.

5. The method of claim 3 wherein the 2,4-D is applied at a rate of from 0.25 to 0.5 pounds per acre.

6. The method of claim 1 wherein the 2,4-D is employed in the form of its dimethylamine salt.

7. The method of claim 1 wherein the *sorghum* is *sorghum bicolor*.

8. The method of claim 1 wherein the mixture of 2,4-D Amine and fluthiacet-methyl is applied as a tank mixture.

9. The method of claim 1 wherein the mixture of 2,4-D Amine and fluthiacet-methyl is applied as a pre-mix.

10. The method of claim 1 wherein the 2,4-D Amine and fluthiacet-methyl are applied separately and sequentially.

11. The method of claim 1 wherein the *sorghum* crop is at least 4 inches tall.

\* \* \* \* \*